United States Patent
Chau et al.

(10) Patent No.: US 10,351,524 B2
(45) Date of Patent: Jul. 16, 2019

(54) HYDROCARBYL CARBOXYBETAINE AND METHOD FOR PREVENTING HOFMANN ELIMINATION IN ALKALINE ENVIRONMENT

(71) Applicant: NATIONAL CHUNG CHENG UNIVERSITY, Chia-Yi (TW)

(72) Inventors: Lai-Kwan Chau, Chiayi (TW); Chun-Jen Huang, Changhua (TW); Wen-Hao Chen, New Taipei (TW); Chao-Wen Chen, Tainan (TW)

(73) Assignee: National Chung Cheng University, Chia-Yi (TW)

( * ) Notice: Subject to any disclaimer, the term of this patent is extended or adjusted under 35 U.S.C. 154(b) by 404 days.

(21) Appl. No.: 15/197,138

(22) Filed: Jun. 29, 2016

(65) Prior Publication Data

US 2017/0001956 A1    Jan. 5, 2017

(30) Foreign Application Priority Data

Jul. 1, 2015 (TW) ................. 104121415 A
Jan. 13, 2016 (TW) ................. 105100991 A (51) Int. Cl.
*C07C 323/25* (2006.01)

(52) U.S. Cl.
CPC ................. *C07C 323/25* (2013.01)

(58) Field of Classification Search
CPC ................. C07C 323/25; C03C 17/00
See application file for complete search history.

(56) References Cited

U.S. PATENT DOCUMENTS

| | | | |
|---|---|---|---|
| 9,394,435 B2* | 7/2016 | Jiang | A61K 41/0019 |
| 2011/0305872 A1* | 12/2011 | Li | A61L 29/06 |
| | | | 428/141 |
| 2013/0274170 A1* | 10/2013 | Yuan-Huffman | A61Q 19/00 |
| | | | 510/337 |
| 2017/0362458 A1* | 12/2017 | Cheng | C07C 229/12 |

FOREIGN PATENT DOCUMENTS

JP          05025106 A   *   2/1993

* cited by examiner

*Primary Examiner* — Cachet I Sellman
(74) *Attorney, Agent, or Firm* — Wang Law Firm, Inc.

(57) ABSTRACT

A Hydrocarbyl Carboxybetaine represented by Formula (1) is provided:

Formula (1)

wherein, $n_1 \geq 0$ and $n_2 > 0$, A is a C1-C20 alkyl group when $n_1 > 0$, and A is a single bond when $n_1 = 0$. $R_1$, $R_2$, $R_3$, and $R_4$ are each independently selected from hydrogen atom, deuterium atom, C1-C20 alkyl group, C2-C20 alkenyl group and C2-C20 alkynyl group; X is selected from SH, $SOCH_3$, $SCH_3$, $NH_2$, $SiCl_3$, $Si(OCH_3)_3$, $Si(OCH_2CH_3)_3$, (Continued)

6 Claims, 8 Drawing Sheets

HYDROCARBYL CARBOXYBETAINE AND METHOD FOR PREVENTING HOFMANN ELIMINATION IN ALKALINE ENVIRONMENT

CROSS-REFERENCE TO RELATED APPLICATION

This application claims priority from Taiwan Patent Application No. 104121415, filed on Jul. 1, 2015, and No. 105100991, filed on Jan. 13, 2016 in the Taiwan Intellectual Property Office, the content of which is hereby incorporated by reference in its entirety for all purposes.

BACKGROUND OF THE INVENTION

1. Field of the Invention

The present disclosure relates to a compound and a method of modifying a biomaterial, particularly relates to a hydrocarbyl carboxybetaine and a method of modifying biomaterials using the same.

2. Description of the Related Art

Figure 1:
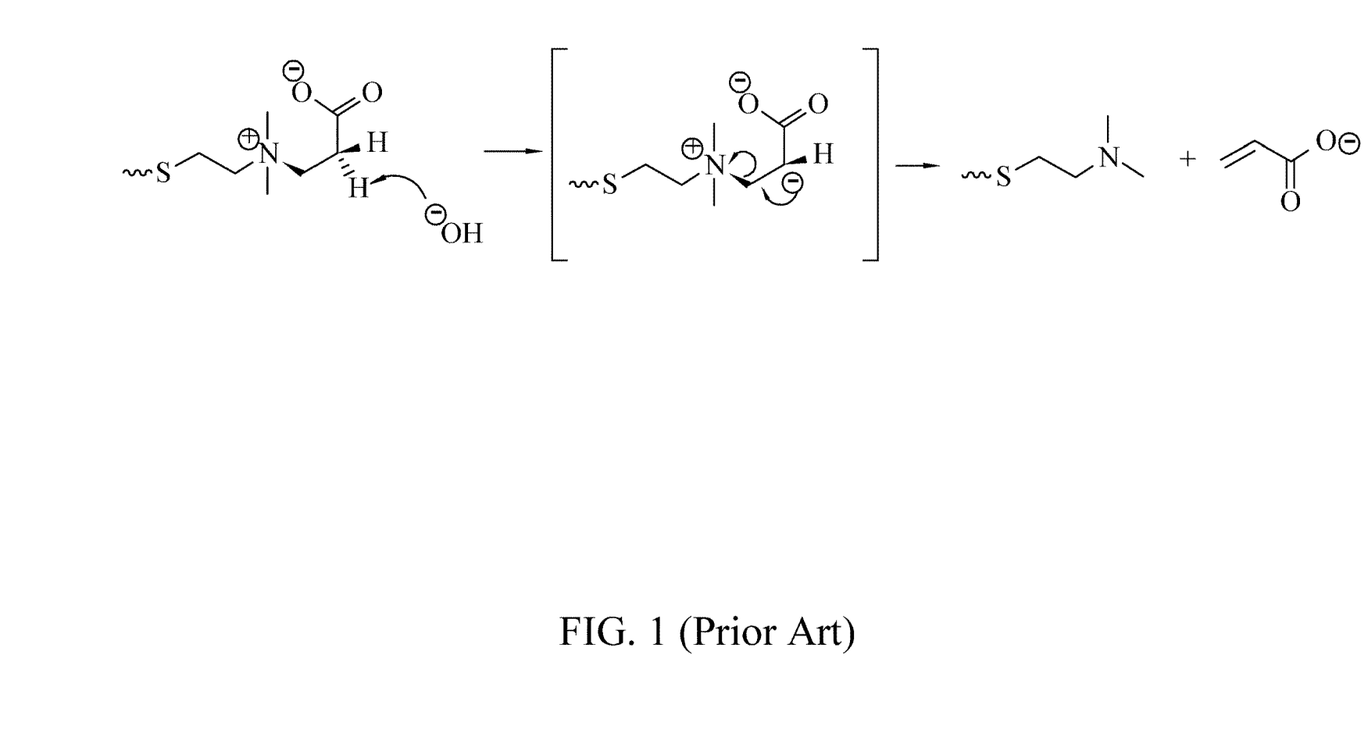
FIG. 1 is a schematic diagram illustrating the process of Hofmann elimination between carboxybetaine of the prior art and the hydroxyl group in the environment.

Conventional carboxybetaine (CB) has excellent ability to resist nonspecific adsorption. However, the molecular stability of the conventional carboxybetaine is less satisfactory. As shown in FIG. 1, the hydrogen bonded to the alpha carbon relative to the carboxyl group in carboxybetaine tends to react with the hydroxyl group in the environment and result in Hofmann elimination. Therefore, the stability of the carboxybetaine in alkaline environment is poor.

SUMMARY OF THE INVENTION

In view of the aforementioned technical problems of the prior art, one purpose of the present disclosure is to provide the hydrocarbyl carboxybetaine capable of preventing Hofmann elimination in alkaline environment and a method of modifying biomaterials using the hydrocarbyl carboxybetaine.

In order to accomplish the preceding purpose, the present disclosure provides hydrocarbyl carboxybetaine capable of preventing Hofmann elimination in alkaline environment, Formula (1)

in which, $n_1 \geq 0$ and $n_2 > 0$, A is a C1-C20 alkyl group when $n_1 > 0$, and A is a single bond when $n_1 = 0$; each of $R_1$, $R_2$, $R_3$, and $R_4$ is independently selected from hydrogen atom (H), deuterium atom (D), C1-C20 alkyl group, C2-C20 alkenyl group and C2-C20 alkynyl group; X is selected from SH, $SOCH_3$, $SCH_3$, $NH_2$, $SiCl_3$, $Si(OCH_3)_3$, $Si(OCH_2CH_3)_3$, In accordance with an objective of the present disclosure, a method of modifying a biomaterial is provided, which includes forming a self-assembled nano thin film on a biomaterial. Wherein, the self-assembled nano thin film is formed from the hydrocarbyl carboxybetaine mentioned above.

In accordance with the preceding descriptions, the hydrocarbyl carboxybetaine capable of preventing Hofmann elimination in alkaline environment and a method of modifying biomaterials using the same of the present disclosure may have one or more advantages listed below:

(1) Due to the effect of steric hindrance, the hydrocarbyl carboxybetaine of the present disclosure can hardly react with hydroxyl group in the environment, and thus the stability of the hydrocarbyl carboxybetaine is promoted in alkaline environment.

(2) The biomaterial modified by the hydrocarbyl carboxybetaine of the present disclosure may possess better ability to resist nonspecific adsorption.

(3) The biomaterial modified by the hydrocarbyl carboxybetaine of the present disclosure may still possess formidable ability to resist nonspecific adsorption even after being treated with the alkaline solution.

DETAILED DESCRIPTION OF THE PREFERRED EMBODIMENTS

The "C1-C20 alkyl group" applied in the present disclosure refers to the linear, branched or cyclic aliphatic monovalent hydrocarbons having 1 to 20 carbon atoms in the main chain thereof. And the C1-C20 alkyl group may include methyl, ethyl, propyl, isobutyl, sec-butyl, tert-butyl, pentyl, isopentyl, hexyl, cyclopropyl, cyclobutyl, cyclopentyl, cyclohexyl and cycloheptyl, but it shall be not limited thereto.

The "C2-C20 alkenyl group" applied in the present disclosure refers to a hydrocarbon group including at least one carbon-carbon double bond at one or more positions along a hydrocarbon chain of the C2-C20 alkyl group, e.g. in the middle or at the end of the C2-C20 alkyl group. C2-C20 alkenyl group may include ethenyl, propenyl, butenyl, cyclopentenyl, cyclohexenyl and cycloheptenyl, but it shall be not limited thereto.

The "C2-C20 alkynyl group" applied in the present disclosure refers to a hydrocarbon group including at least one carbon-carbon triple bond at one or more positions along a hydrocarbon chain of the C2-C20 alkyl group, e.g. in the middle or at the end of the C2-C20 alkyl group. C2-C20 alkynyl group may include ethynyl, propynyl and the cyclooctynyl, but it shall be not limited thereto.

The "biomaterial" applied in the present disclosure refers to the materials applied extensively to biological system, including but not limited to metals, ceramics and polymeric materials such as titanium, silicons, teflon, nylon, etc.

The "modify" applied in the present disclosure refers to physical or chemical modification, which may include physical vapor deposition (PVD), chemical vapor deposition (CVD), electrochemical deposition and sol gel process, but not limited thereto.

The "self-assembled molecule" applied in the present disclosure refers to the special molecules capable of organizing themselves closely without external force. The rate of self-assembly of such molecules may depend on solvents or van der Waals Force between the molecules themselves. Generally, the longer the backbone of the self-assembled molecules is, the more hydrophobic the molecules become, and therefore the faster the molecular self-assembly is. The "self-assembled nano thin film" in the present disclosure includes the aforementioned self-assembled molecule.

The present disclosure provides hydrocarbyl carboxybetaine capable of preventing Hofmann elimination in alkaline environment. The hydrocarbyl carboxybetaine may be represented by the following Formula (1):

Formula (1)

wherein, $n_1 \geq 0$ and $n_2 > 0$. A is a C1-C20 alkyl group when $n_1 > 0$, and A is a single bond when $n_1 = 0$; $R_1$, $R_2$, $R_3$, and $R_4$ are each independently selected from hydrogen atom (H), deuterium atom (D), C1-C20 alkyl group, C2-C20 alkenyl group and C2-C20 alkynyl group; X is selected from SH, $SOCH_3$, $SCH_3$, $NH_2$, $SiCl_3$, $Si(OCH_3)_3$, $Si(OCH_2CH_3)_3$, In the selected embodiment, Formula (1) may be represented by the following Formula (2) or Formula (3):

Formula (2)

Formula (3)

Here, the definitions of $n_1$, $n_2$, A, $R_1$, $R_2$, $R_3$, $R_4$ and X in Formula (2) and Formula (3) are same as that in Formula (1). In a selected embodiment, $n_1 = 0$ in Formula (3) and one of $R_3$ and $R_4$ is C1-C20 alkyl group while the other is a hydrogen atom. Preferably, one of $R_3$ and R4 may be methyl group and the other may be a hydrogen atom. In another selected embodiment, $n_1 = 0$ in Formula (2) and one of $R_1$ and $R_2$ is C1-C20 alkyl group while the other is a hydrogen atom. Preferably, one of $R_1$ and $R_2$ is methyl group, and the other is a hydrogen atom.

In the selected embodiment, the definitions of $n_1$, $n_2$, A, $R_1$, $R_2$, $R_3$, $R_4$ and X are same as that in Formula (2) and Formula (3).

Figure 2:
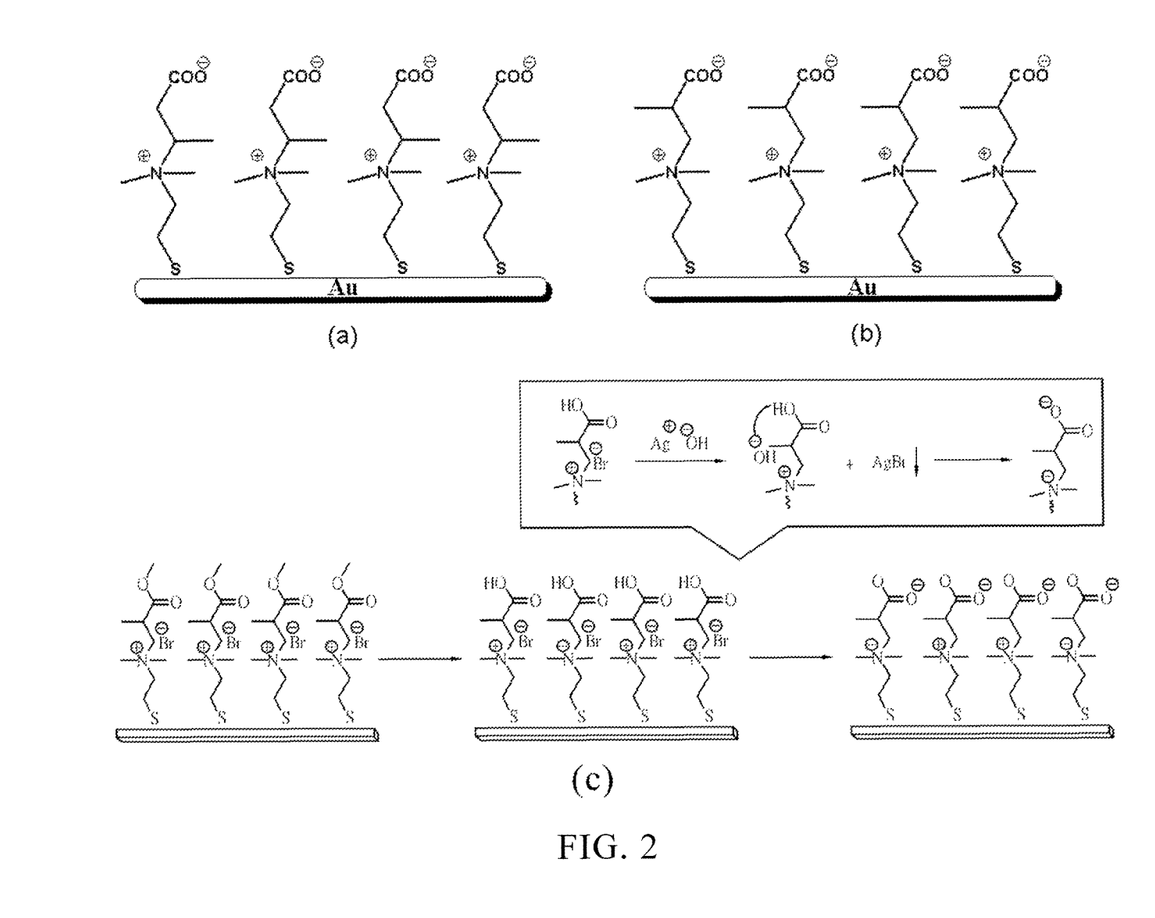
FIG. 2 is a schematic diagram illustrating the modification of hydrocarbyl carboxybetaine on the nano-gold surface according to an embodiment of the present invention.

In the selected embodiment, the hydrocarbyl carboxybetaine represented by Formula (1) is Because the hydrocarbyl carboxybetaine of the present disclosure is a self-assembled molecule, when being modified on a biomaterial, the hydrocarbyl carboxybetaine autonomously forms a self-assembled nano thin film on the biomaterial as shown in FIG. 2(a) and FIG. 2(b). The hydrocarbyl carboxybetaine of the present disclosure can be directly modified on the biomaterial, or can be modified on the biomaterial by using the hydrocarbyl carboxybetaine containing the protecting group as shown in FIG. 2(c). The modification on the biomaterial includes the following steps:

(1) producing the hydrocarbyl carboxybetaine containing the protecting group of the present disclosure, which could be carboxy-alpha-methyl-betaine methyl ester or carboxy-beta-methyl-betaine methyl ester;

(2) modifying the hydrocarbyl carboxybetaine containing the protecting group on the biomaterial;

(3) removing the protecting group from the hydrocarbyl carboxybetaine containing the protecting group; and

(4) performing an ion-exchange reaction to the deprotected hydrocarbyl carboxybetaine.

The following paragraphs will detail the present disclosure with reference to the synthesized embodiments.

Synthesized Embodiment 1: Preparation of Compound 1

Equation 1

2-hydroxyethyl disulfide (1.55 g, 10 mmol) and triethylamine (2.5 g, 25 mmol) are dissolved in dichloromethane, and then MsCl (2.5 g, 22 mmol) is added to the solution, and the solution is allowed to react at a temperature of 0° C. for 30 minutes. After that, the reactant is concentrated under vacuum, and then citric acid solution (100 ml, 10% v/v) is added. Next, the concentrated liquid is extracted twice with dichloromethane (2×, 100 ml), and the organic layer is extracted twice with sodium bicarbonate solution (2×, 100 ml). Subsequently, sodium sulfate is used to dry and concentrate the organic layer to obtain yellow greasy 2-methylsulfonyl-ethyl disulfide.

The obtained yellow greasy 2-methylsulfonyl-ethyl disulfide (2.8 g, 10 mmol) is added to dimethylamine solution in THF (25 ml, 1M) and allowed to react at the room temperature for 8 hours. Then the product is concentrated under vacuum. NaOH solution (200 ml, 2M) is added and the product is twice extracted with dichloromethane (2×200 ml). Subsequently sodium sulfate is used to dry the organic layer, and then the product is filtered and concentrated to obtain black greasy N,N-dimethyl-ethyl disulfide. Here, the yield is 90%.

The obtained black greasy N,N-dimethyl-ethyl disulfide (2.1 g and 10 mmol) is dissolved in (R)-(+)-3-(R)-(+)-3-bromoisobutyric acid methyl ester and anhydrous acetonitrile (4.5 g and 25 mmol), the solution is stirred and allowed to react at a temperature of 60° C. for 16 hours. After the reaction, a solid is obtained. Then the solid is washed for three times with ether and then the yellow greasy substance is obtained by vacuum drying. The yellow greasy substance is reacted with TFA solution (TFA: $H_2O$=99:1) for 15 minutes at room temperature, and then TFA is removed by vacuum drying. After that, $Ag_2O$ saturated solution is added to dissolve the solid and the insoluble substance is removed by filtering. The solution is dried by vacuum drying to obtain the yellow solid Compound 1 i.e. carboxy-alpha-methyl-betaine disulfide (α-mCB disulfide), whereby the yield is 74%.

Synthesized Embodiment 2: Preparation of Compound 2

Equation 2

2-hydroxyethyl disulfide (1.55 g, 10 mmol) and triethylamine (2.5 g, 25 mmol) are dissolved in dichloromethane, and then MsCl (2.5 g, 22 mmol) is added to the solution, the solution is allowed to react at temperature of 0° C. for 30 minutes. After that, the reactant is concentrated under vacuum, and citric acid solution (100 ml and 10% v/v) is added. Next, the concentrated liquid is extracted twice with dichloromethane (2×, 100 ml), and the organic layer is extracted twice with sodium bicarbonate solution (2×, 100 ml). Then, sodium sulfate is used to dry and concentrate the organic layer to obtain yellow greasy 2-methylsulfonyl-ethyl disulfide. The yellow greasy 2-methylsulfonyl-ethyl disulfide (2.8 g, 10 mmol) is added to dimethylamine solution in THF (25 ml, 1M), and then allowed to react at room temperature for 8 hours. After that, the product is concentrated under vacuum, NaOH solution (200 ml, 2M) is added and dichloromethane is used to extract the product for two times (2×200 ml). Sodium sulfate is used to dry the organic layer, and then the product is filtered and concentrated to obtain black greasy N,N-dimethyl-ethyl disulfide.

N,N-dimethyl-ethyl disulfide of 2.33 M and β-butyrolactone of 3.5 M are mixed in anhydrous acetonitrile at a temperature of 0° C. After 20 minutes, the product is moved to room temperature and allowed to react for three days, and a white solid product is obtained. After the obtained white solid product is washed with acetone for three times, and subsequently dissolved in ethanol, acetone is added, such that a white solid is produced from the recrystallization. After filtration and vacuum drying, the white powder is finally obtained, i.e. carboxy-beta-methyl-betaine disulfide (β-mCB disulfide), Compound 2.

The Compounds 1 and 2 mentioned above are used as an exemplary embodiment. The modification of these two compounds on the nano-gold surface is illustrated in the context hereafter and FIG. 2.

Embodiment 1 the optical fiber modified by nano-gold is washed, and the organic impurities on the surface thereof are removed by oxygen plasma. Then, the optical fiber is modified by soaking in DMSO solution containing Compound 1 (1 mM concentration) at room temperature for 12 hours, in order to obtain Substrate 1.

Embodiment 2 the glass substrate coated with gold film is washed, and the organic impurities on the surface thereof are removed by oxygen plasma. Then, the glass substrate is modified by soaking in DMSO solution containing Compound 2 (1 mM concentration) at the room temperature for 12 hours, to obtain Substrate 2.

Test Analysis:

The paragraphs hereinafter will illustrate various tests on the resistance of Substrate 1 against nonspecific adsorption.

Figure 3:
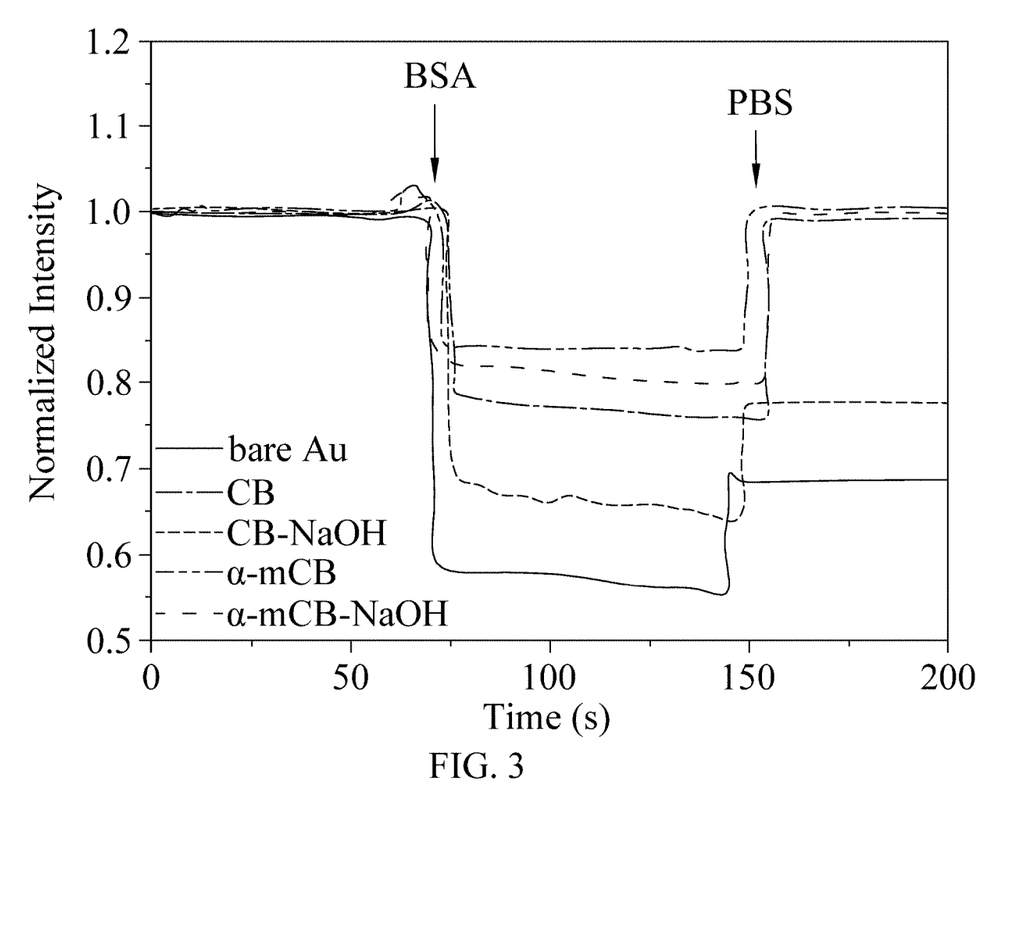
FIG. 3 is the plot showing the results of nonspecific adsorption test for carboxybetaine and carboxy-alpha-methyl-betaine of the present disclosure that are modified on the nano-gold surface, before and after treatment in alkaline solution.

Test 1:

The nonspecific adsorption resistances of the substrates modified by carboxy-alpha-methyl-betaine of the present invention and carboxybetaine, before and after the treatment of 1M NaOH, are respectively tested in the optical fiber bio-sensing system and the experiment result is displayed in FIG. 3. As shown in FIG. 3, the bare nano-gold on the surface of the substrate is not modified by any self-assembled nano thin film. As a result, in the test of nonspecific adsorption resistance using highly concentrated (49 mg/ml) bovine serum albumin (BSA), more BSA will be attached on the surface of bare nano-gold if the substrate is rinsed with phosphate buffered saline (PBS). On the other hand, for the substrate modified with self-assembled carboxybetaine (CB) nano thin film of the prior art, the nonspecific adsorption resistance thereof differs significantly before and after the treatment of 1M NaOH solution, owing to the effect of Hofmann elimination. For Substrate 1 modified with the self-assembled hydrocarbyl carboxybetaine (α-mCB) nano thin film of the present disclosure, there is no evident difference between the nonspecific adsorption resistance of Substrate 1 before and after the treatment of 1M NaOH solution. Therefore, in the present invention, since one or two hydrogen atoms bonded to the carbon chain of the carboxyl group of carboxybetaine is substituted with C1-C20 alkyl group, C2-C20 alkenyl group or C2-C20 alkynyl group, and the steric hindrance of the substituted C1-C20 alkyl group, C2-C20 alkenyl group or C2-C20 alkynyl group is greater than that of hydrogen atom, it is hard to react with the hydroxyl group in the environment. Thus, Hofmann elimination can be avoided, and the stability of hydrocarbyl carboxybetaine of the present invention in alkaline environment can be improved.

Figure 4:
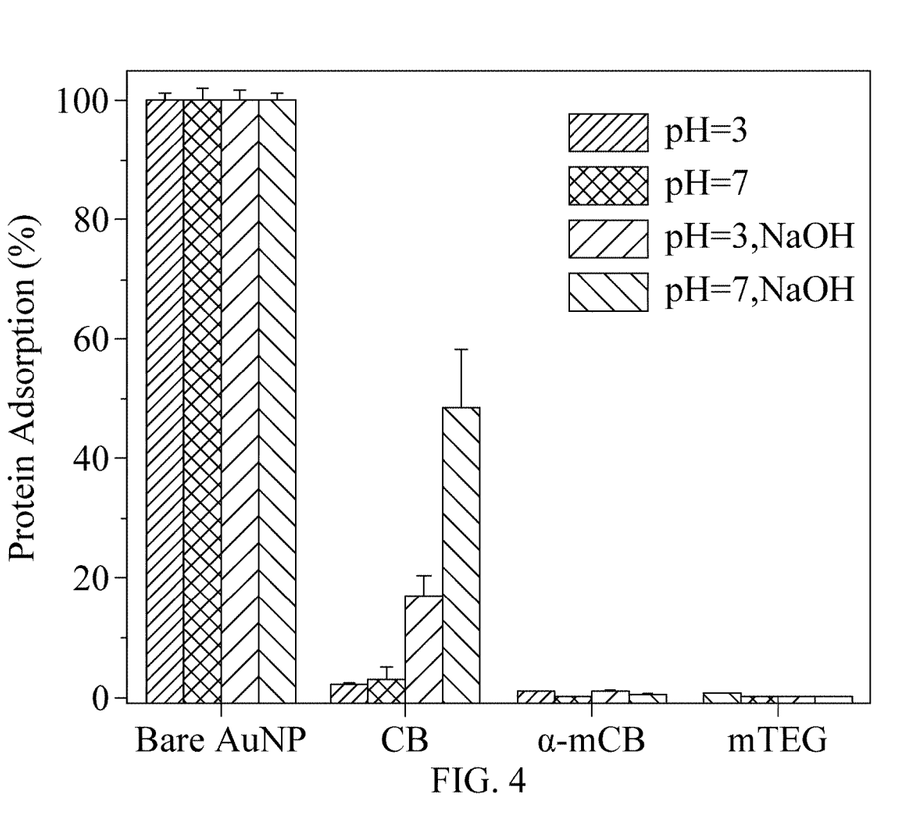
FIG. 4 is the bar chart showing the results of nonspecific adsorption test for carboxybetaine and carboxy-alpha-methyl-betaine of the present disclosure against BSA, before and after being treated with 1M NaOH, in buffer solution of different pH.

Test 2:

The test of protein adsorption is conducted with the optical fiber bio-sensing system. In the test, 49 mg/ml of bovine serum albumin (BSA) is formulated in the PBS solution. The PBS is used to remove the protein solution after the protein solution contacts with the substrate surface for approximately 90 seconds. FIG. 4 shows the test results of the nonspecific adsorption resistances of the self-assembled nano thin film of carboxybetaine (CB), hydrocarbyl carboxybetaine of the present invention (α-mCB in this case) and the commercially-available TEG containing thiol, before and after the treatment of 1M NaOH, for different pH values. According to the test it can be found that the nonspecific adsorption resistance of the self-assembled nano thin film of carboxybetaine has apparently declined after being treated with NaOH. Whereas for different pH values, the BSA adsorption on the self-assembled nano thin film of carboxybetaine differs significantly. By comparison, it can be found that the self-assembled nano thin film of hydrocarbyl carboxybetaine of the present disclosure does not undergo Hofmann elimination. Regardless of pH of the solutions, the highly hydrophilic zwitterionic nano thin film formed from hydrocarbyl carboxybetaine of the present disclosure can be found on the surface of the Substrate 1, thereby endowing the substrate with high nonspecific adsorption resistance. Regardless of the charge on the BSA surface, the self-assembled nano thin film of hydrocarbyl carboxybetaine of the present invention is capable to repel BSA. Thus, the present invention has excellent nonspecific adsorption resistance.

Conventionally, the self-assembled nano thin film of TEG is applied as the primary structure to resist nonspecific adsorption. This is due to the fact that the structure of TEG carries neither positive nor negative charge. So, the nonspecific adsorption resistance thereof is not affected by pH values, and the experiment results verify that the self-assembled nano thin film of TEG exhibit excellent nonspecific adsorption resistance in different pH values.

Test 3:

Sodium acetate aqueous solution is added, and when the signal becomes stable, the mixed solution of EDC/NHS is added. At this moment, the refractive index changes significantly, so there is an apparent variation in the signal. Meanwhile, EDC will activate the carboxyl group of the hydrocarbyl carboxybetaine on the surface of Substrate 1 and then NHS will bond to the activated carboxyl group by esterification reaction. After a while, deionized water is used to wash away residual EDC/NHS on the surface, and then an antibody solution formulated with HEPES is injected. The substrate is left undisturbed for a few minutes to allow the reaction to take place. During this, the activated carboxyl group will form amide bond with the N-terminus on the antibody molecule, so as to be fixed on Substrate 1. When the reaction is completed, Substrate 1 is washed with aqueous sodium bicarbonate solution, as the alkaline environment provided by sodium bicarbonate induces elimination reaction of NHS from carboxyl group, so as to achieve the purpose of deactivation. Finally, after stabilizing the signal with PBS buffer solution, solutions of the corresponding antigen of increasing concentration are injected to perform the bio-sensing. When the test is completed, the stabilized signal of the PBS buffer solution is used as an initial signal to respectively process each signal generated by the antigen with different concentrations. The signals corresponding to the concentrations are plotted in FIG. 5.

Figure 5:
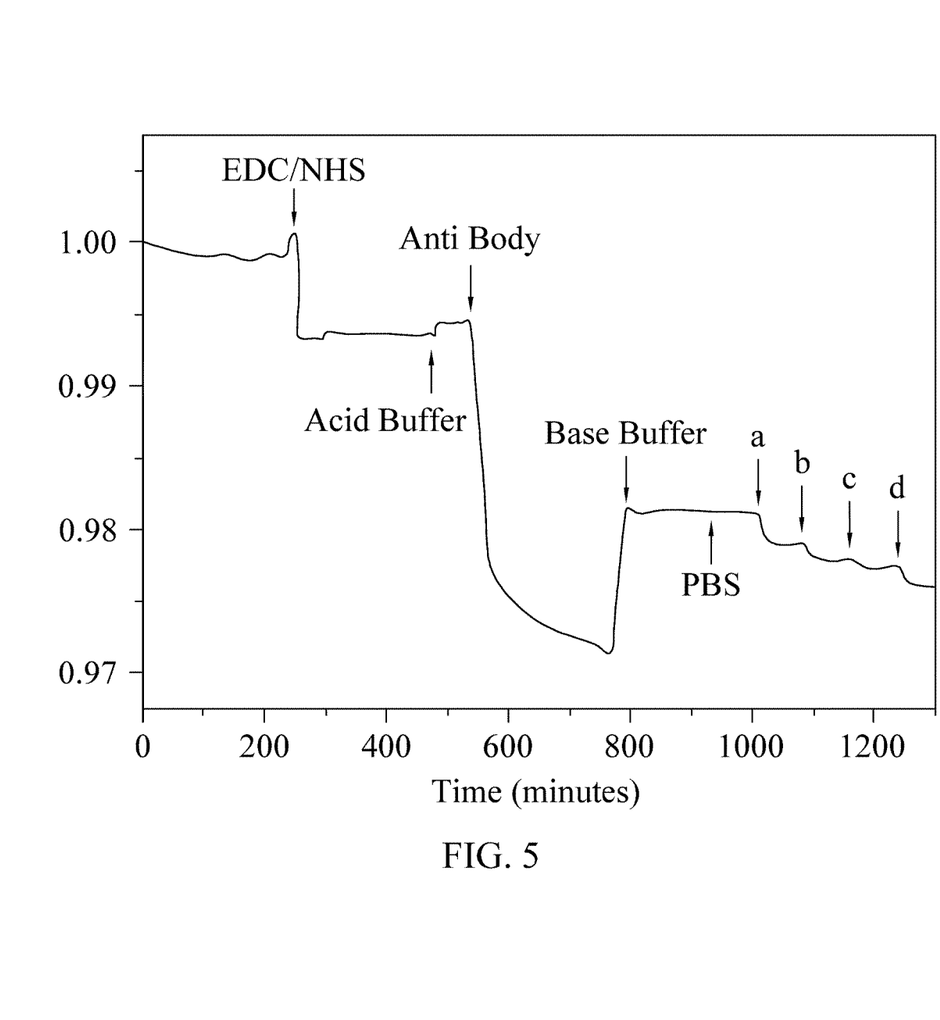
FIG. 5 is the plot showing the real-time detection signals of the bio-sensing performed on carboxy-alpha-methyl-betaine of the present disclosure modified by an antibody, after modification on the nano-gold surface.
Figure 6:
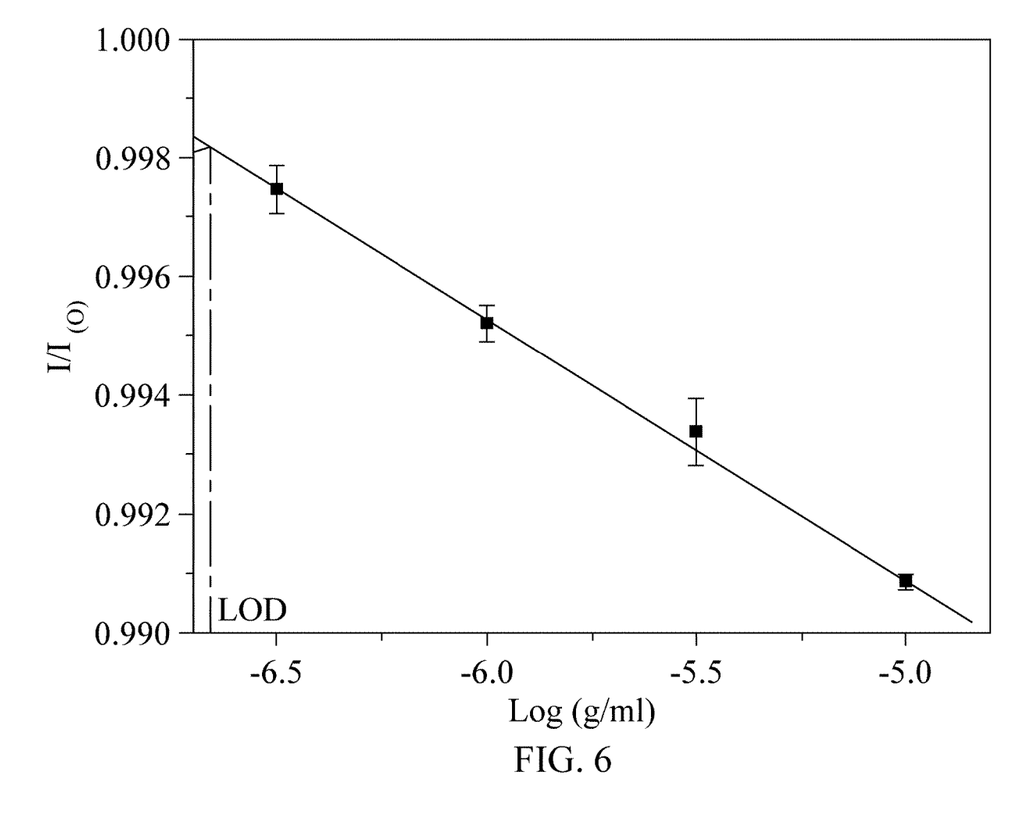
FIG. 6 is a plot showing the normalized data of FIG. 5.

Since the hydrocarbyl carboxybetaine of the present disclosure has both the nonspecific adsorption resistance and stable molecular structure, only a monolayer of self-assembled molecule is required in order to achieve the modification of functionalized film. As shown in FIG. 5, after the antibody is modified on the self-assembled monolayer of hydrocarbyl carboxybetaine (α-mCB) of the present disclosure by amide bond using 1-ethyl-3-(3-dimethylaminopropyl)carbodiimide/N-hydroxysuccinimide (EDC/NHS), the optical fiber of the hydrocarbyl carboxybetaine conjugated with antibody still produces satisfactory bio-sensing results. After normalizing the data of FIG. 5, a linear relationship diagram can be obtained, as shown in FIG. 6. In FIG. 6, the limit of detection (LOD) of the hydrocarbyl carboxybetaine of the present disclosure is $1.8 \pm 0.6 \times 10^{-7}$ g/ml.

Figure 7:
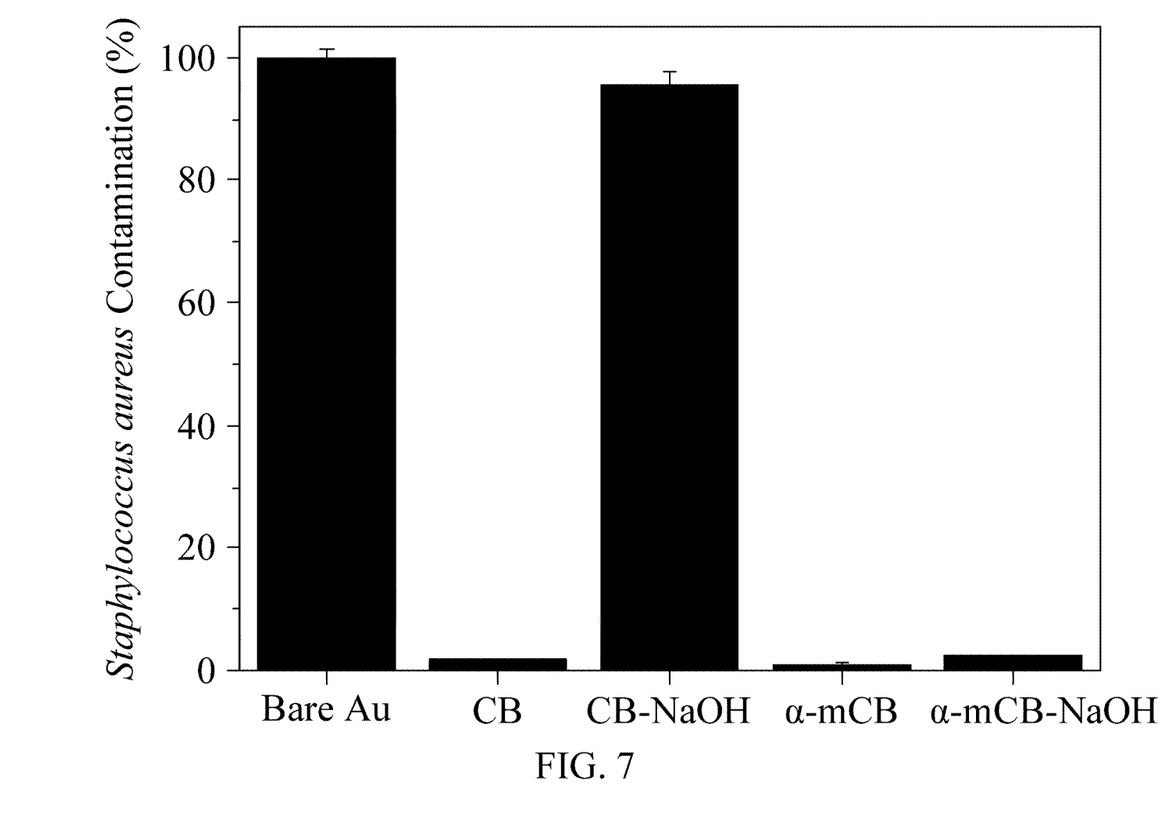
FIG. 7 is a bar chart showing anti-biofouling test results of carboxy-alpha-methyl-betaine of the present disclosure and carboxybetaine modified on the surface of gold film, against *Staphylococcus aureus*.

FIG. 7 is a bar chart showing anti-biofouling test results of carboxy-alpha-methyl-betaine of the present disclosure and carboxybetaine modified on the surface of gold film, against *Staphylococcus aureus*. In FIG. 7, compared to conventional carboxybetaine (CB) treated with 1M NaOH (CB-NaOH), carboxy-alpha-methyl-betaine treated with 1M NaOH (α-mCB-NaOH) exhibits better adsorption resistance against the biofouling of *S. aureus*.

Figure 8:
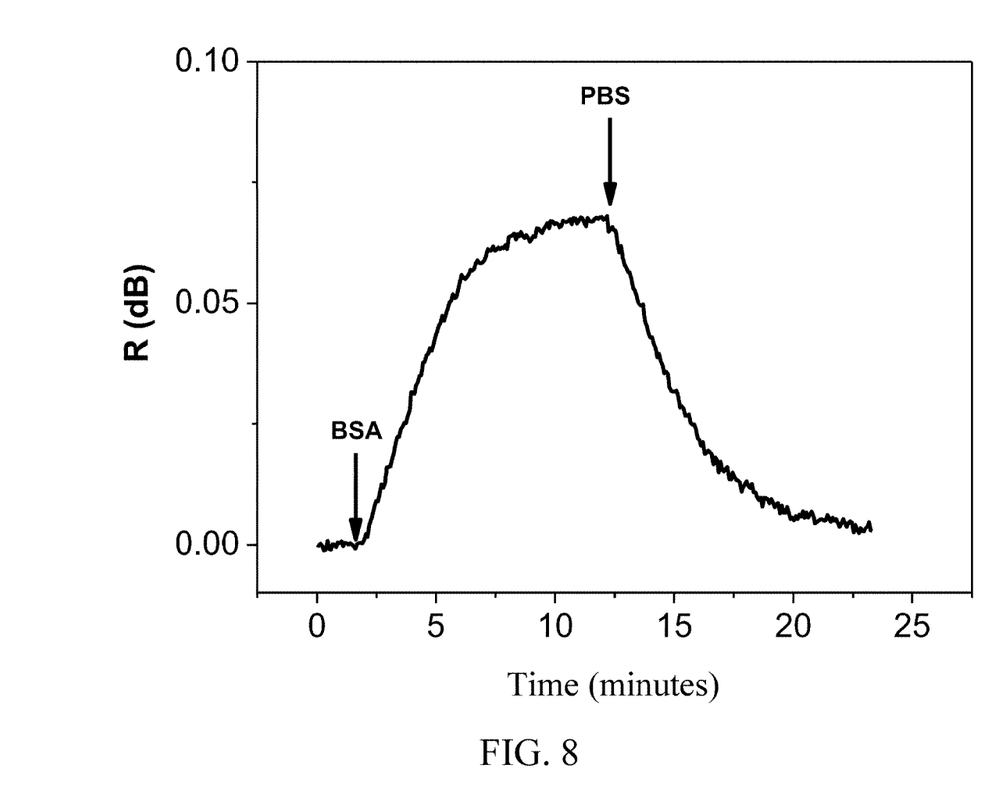
FIG. 8 is a plot showing anti-biofouling test results of carboxy-beta-methyl-betaine of the present disclosure modified on the surface of gold film, against BSA.

FIG. 8 is a plot showing anti-biofouling test results of carboxy-beta-methyl-betaine of the present disclosure modified on the surface of gold film, against BSA. The Substrate 2 (as shown in FIG. 2(a)) is placed in the SPR biosensor to perform the test of nonspecific adsorption for BSA protein. After 10 minutes of protein adsorption, PBS buffer solution is used to wash Substrate 2. As shown in FIG. 8, it can be found that BSA is removed from the surface, so that protein is prevented from adhering to Substrate 2. As a result, carboxy-beta-methyl-betaine of the present disclosure has better nonspecific adsorption resistance.

Being the zwitterionic material, carboxybetaine possesses excellent resistance against nonspecific adsorption of biological matters. According to the experiments mentioned above, it can be found that the hydrocarbyl carboxybetaine of the present invention is able to prevent Hofmann elimination in alkaline environment. Hence, in contrast to carboxybetaine, hydrocarbyl carboxybetaine of the present invention not only has equally excellent resistance against nonspecific adsorption of biological matters, but also better stability in alkaline environment. The hydrocarbyl carboxybetaine of the present disclosure is therefore applicable to the modification of biomaterial, such that the excellent nonspecific adsorption resistance thereof can be maintained even in alkaline environment. As a result, when the biomaterial comes into contact with blood, plasma protein adsorption or platelet adhesion that frequently occurs between the blood and the biomaterial can be avoided, as such occurrence will cause the loss of functionality of the biomaterial.

While the means of specific embodiments in present disclosure has been described by reference drawings, numerous modifications and variations could be made thereto by those skilled in the art without departing from the scope and spirit of the disclosure set forth in the claims. The modifications and variations should in a range limited by the specification of the present disclosure.

What is claimed is:

1. Hydrocarbyl carboxybetaine represented by Formula (1) below:

Formula (1)

wherein, $n_1 \geq 0$ and $n_2 > 0$;

A is C1-C20 alkyl group when $n_1 > 0$, and A is a single bond when $n_1 = 0$;

$R_1$, $R_2$, $R_3$, and $R_4$ are each independently selected from hydrogen atom, deuterium atom, C1-C20 alkyl group, C2-C20 alkenyl group and C2-C20 alkynyl group; and X is selected from SH, $SOCH_3$, $SCH_3$, $NH_2$, $SiCl_3$, $Si(OCH_3)_3$, $Si(OCH_2CH_3)_3$, $Y_1 = O, S, CH_2$
$Y_2 = SH, SOCH_3, SCH_3$ $m > 0$ 2. The hydrocarbyl carboxybetaine of claim 1, wherein Formula (1) is represented by Formula (2) or Formula (3) below:

wherein, $n_1$, $n_2$, A, $R_1$, $R_2$, $R_3$, $R_4$ and X are defined in a same way as Formula (1).

3. The hydrocarbyl carboxybetaine of claim 2, wherein $n_1=0$, one of $R_1$, $R_2$, $R_3$ and $R_4$ is C1-C20 alkyl group, and the remainder are hydrogen atoms.

4. The hydrocarbyl carboxybetaine of claim 2, wherein one of $R_1$, $R_2$, $R_3$ and $R_4$ is methyl group, and the remainder are hydrogen atoms.

5. The hydrocarbyl carboxybetaine of claim 2, wherein X is

6. The hydrocarbyl carboxybetaine of claim 1, wherein the hydrocarbyl carboxybetaine represented by Formula (1) is

* * * * *